United States Patent [19]
Andrews et al.

[11] Patent Number: 5,914,125
[45] Date of Patent: *Jun. 22, 1999

[54] WOUND DRESSING

[75] Inventors: Trevor John Andrews, Ashford; Graham John Collyer, Padfield, both of United Kingdom

[73] Assignee: Ultra Laboratories Limited, Oldham, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/892,174

[22] Filed: Jul. 14, 1997

Related U.S. Application Data

[62] Continuation of application No. 08/433,950, May 4, 1995, abandoned, which is a continuation of application No. 08/098,336, filed as application No. PCT/GB92/00231, Feb. 7, 1992, abandoned.

[30] Foreign Application Priority Data

Feb. 7, 1991 [GB] United Kingdom .................... 9102660

[51] Int. Cl.⁶ ....................................................... A61F 13/00
[52] U.S. Cl. ............................................. 424/443; 424/445
[58] Field of Search ...................................... 424/443, 445

[56] References Cited

U.S. PATENT DOCUMENTS

| | | | |
|---|---|---|---|
| 3,653,383 | 4/1972 | Wise | 128/296 |
| 3,978,855 | 9/1976 | McRae | 428/311 |
| 4,127,124 | 11/1978 | Clagett | 128/165 |
| 4,191,815 | 3/1980 | Jourquin et al. | 521/51 |
| 4,550,126 | 10/1985 | Lorenz | 521/159 |
| 4,664,662 | 5/1987 | Webster | 604/369 |

FOREIGN PATENT DOCUMENTS

| | | |
|---|---|---|
| 0041934 | 12/1981 | European Pat. Off. |
| 0053936 | 6/1982 | European Pat. Off. |
| 0092999 | 11/1983 | European Pat. Off. |
| 0117438 | 9/1984 | European Pat. Off. |
| 0196364 | 10/1986 | European Pat. Off. |
| 0209142 | 1/1987 | European Pat. Off. |
| 0267051 | 5/1988 | European Pat. Off. |
| 0272918 | 6/1988 | European Pat. Off. |
| 0279118 | 8/1988 | European Pat. Off. |
| 0299122 | 1/1989 | European Pat. Off. |
| 0327328 | 8/1989 | European Pat. Off. |
| 0335669 | 10/1989 | European Pat. Off. |
| 0629419 | 9/1949 | United Kingdom . |
| 0696309 | 8/1953 | United Kingdom . |
| 0816854 | 7/1959 | United Kingdom . |
| 1001912 | 8/1965 | United Kingdom . |
| 1306508 | 2/1973 | United Kingdom . |
| 1378931 | 12/1974 | United Kingdom . |
| 1417962 | 12/1975 | United Kingdom . |
| 1570485 | 7/1980 | United Kingdom . |
| 2048070 | 12/1980 | United Kingdom . |
| 1583367 | 1/1981 | United Kingdom . |
| 1594389 | 7/1981 | United Kingdom . |
| 1602858 | 11/1981 | United Kingdom . |
| 2083487 | 3/1982 | United Kingdom . |
| 2093702 | 9/1982 | United Kingdom . |
| 2093703 | 9/1982 | United Kingdom . |
| 2102012 | 1/1983 | United Kingdom . |
| 2134792 | 8/1984 | United Kingdom . |
| 2207865 | 2/1989 | United Kingdom . |
| 2221620 | 1/1990 | United Kingdom . |
| 2228682 | 9/1990 | United Kingdom . |

OTHER PUBLICATIONS

Turner, T.D., Proceedings of a Symposium on Wound Healing (Sundell B. ed.) pp. 75–84 (1978).

*Primary Examiner*—D. Gabrielle Brouillette
*Attorney, Agent, or Firm*—Duane, Morris & Heckscher LLP

[57] ABSTRACT

The dressing for heavily exuding wounds comprises a hydrophilic foam having an absorptive capacity of at least 10 times its own weight, such as a hydrophilic polyether polyurethane foam material derived from a foamable composition comprising a polyol component containing ethylene oxide groupings. For use on bleeding wounds and/or to improve the absorptive capacity of the foam itself, the foam may be impregnated with alginate, which acts both as a haemostat and as an absorption improver. The dressing may include a backing layer which provides a barrier to microorganisms.

18 Claims, 2 Drawing Sheets

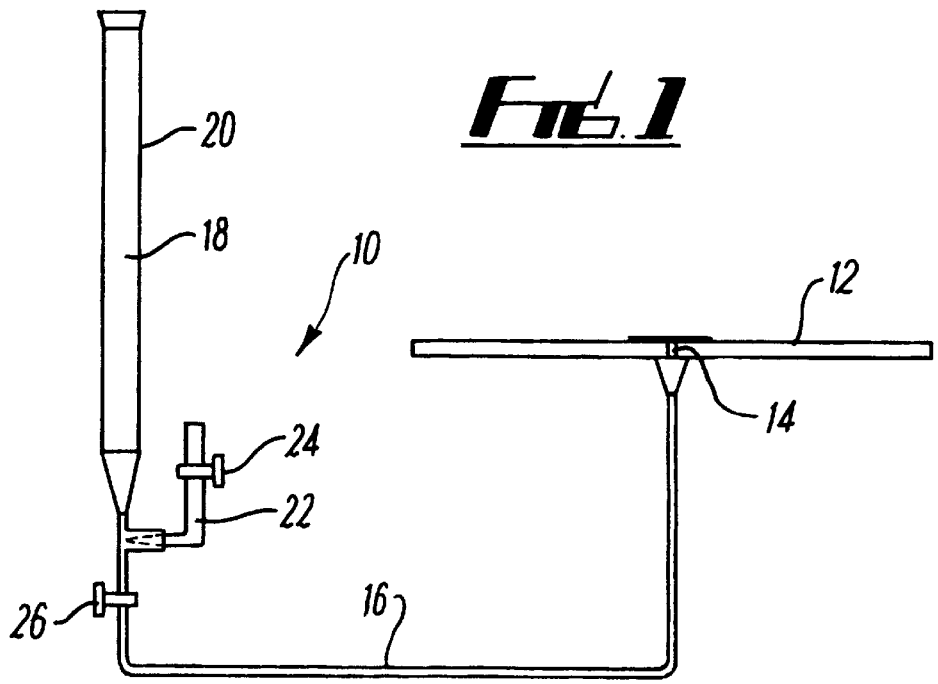
FIG. 1
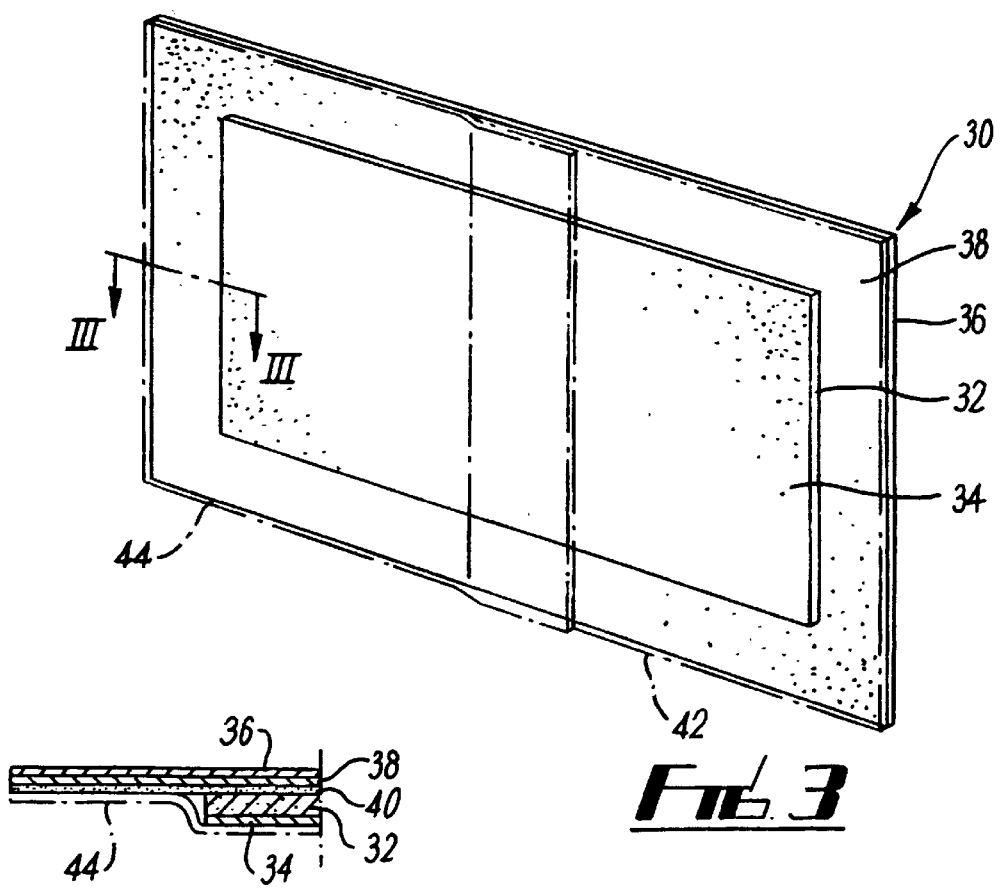
FIG. 3
FIG. 4

WOUND DRESSING

This is a continuation application of application Ser. No. 08/433,950, filed May 4, 1995, now abandoned, which, in turn, is a continuation of application Ser. No. 08/098,336, filed Feb. 3, 1994, now abandoned, which, in turn, is a national stage filing of PCT/GB92/00231, filed on Feb. 7, 1992, which, in turn, is based on United Kingdom Application Ser. No. 9102660.9, filed on Feb. 7, 1991.

BACKGROUND OF THE INVENTION

This invention relates to wound dressings and particularly but not exclusively to such dressings as are useful in the treatment of heavily exuding wounds and in first aid, especially industrial first aid.

The following seven requirements have been specified for an ideal wound dressing, namely that it should:

1. Remove excess exudate away from the wound surface
2. Maintain high humidity at the wound/dressing interface
3. Provide thermal insulation
4. Allow gaseous exchange, and the passage of water vapour
5. Not shed fibres nor leach out toxic substances
6. Be impermeable to microorganisms
7. Not cause trauma during removal from the wound
   [Turner T. D., in Proceedings of a Symposium on Wound Healing (Sundell B.ed) pp 75–84 (1978)]

All but the first of these requirements are fully met by a foam of the type described in the Specification of our UK Patent No 1 417 962, Claim 1 of which is in the following terms:

"A non-reticulated polyurethane foam material, the foam cells adjacent at least one surface of which are irreversibly partially collapsed relative to foam cells remote from said surfaces and which surface is absorbent to aqueous based liquids";

or in the Specification of the Patent of Addition thereto which is directed to a similar, but reticulated, foam material. Such foams are commercially available, being sold under the name LYOFOAM (Registered Trade Mark) and they have achieved widespread acceptance in the treatment of moderately exuding wounds. However, they may not have sufficient absorbency to absorb all the exudate from heavily exuding wounds.

Accordingly there is still a need for a dressing with sufficient absorbency for use on heavily exuding wounds, and it is an aim of the present invention to provide such a dressing.

Various methods investigated by the Applicants to achieve a higher absorbency foam dressing were found to be attended by certain drawbacks. The incorporation of a surfactant during manufacture of the foam did achieve slightly increased Absorbency but posed problems with regard to the presence of free surfactant in the final product and in achieving adherence of a backing layer which is often necessary to exclude bacterial infection.

The incorporation of an alginate during manufacture of the foam was attended by degradation of the alginate (a polysaccharide) and consequent impairment of its absorbent and haemostatic properties and also deterioration in the appearance of the foam.

SUMMARY OF THE INVENTION

However, it has been found that a polyether polyurethane foam formed from a composition in which the polyol components are rich in ethylene oxide could provide a foam that had the required high absorption characteristics, and according to the present invention there is provided a wound dressing comprising a physiologically-compatible, open-celled foam material having an absorptive capacity greater than 10 times its own weight.

The important ingredients in a hydrophilic polyether polyurethane foam are two different classes of polyol, namely a polyether polyol rich in ethylene oxide i.e., having 70–80% ethylene oxide groups, (Polyol 1) and a branched ethylene oxide modified polyether polyol (Polyol 2). A Polyol 1/Polyol 2 ratio of from 65:35 to 85:15 parts by weight is preferred for giving a polyether polyurethane foam suitable for use in the present invention. (By convention in the art of polyurethane foam manufacture the parts by weight of Polyol 1 and 2 total 100.)

A typical foamable composition comprises the following ingredients:

a) Polyether polyol rich in ethylene oxide (Polyol 1)
b) Branched ethylene oxide modified polyether polyol (Polyol 2)
c) Toluene diisocyanate (T80/20)
d) Dimethyl ethanolamine (DMEA)
e) Triethylene diamine (TEDA)
f) Polysiloxane—polyoxyalkylene block copolymer (cell stabiliser)
g) Water or alternative blowing agent The hydrophilic properties of the foam can be varied by adjusting the ethylene oxide content of Polyol 1 or by altering the relative ratios of Polyol 1 and Polyol 2.

For most uses of the dressing it is preferred to modify a surface of the foam by application of heat and pressure to provide the requisite low degree of adherence to the wound. Moreover, this treatment provides a faster rate of absorbency at the treated surface layer in contact with the wound than in the bulk of the foam, thus maintaining the desired high humidity at the wound/dressing interface.

As the body of a polyurethane foam dressing of the 'Lyofoam' type is hydrophobic it provides a bacterial barrier. However, the foam used in the dressing of the present invention is hydrophilic throughout and subject to 'fluid strike-through' which provides a path for entrance of bacteria to the wound. It is therefore essential in most cases that the dressing according to the invention additionally comprises a non-absorbent backing layer which is gas- and vapour-permeable to ensure gaseous exchange and to allow evaporation of the aqueous content of exudate. The backing layer may be adhered by the application of heat and pressure or by a vapor-permeable adhesive -which may a hot-melt, moisture-cure or solvent-based adhesive.

The Applicants have also found that impregnation of certain known foams with an alginate composition will raise the absorptive capacity to a degree suitable for use in the present invention; alginate impregnation of the hydrophilic polyether polyurethane foams described above will clearly further enhance their already high absorptive capacity.

Alginates have, of course, long been recognised as useful in wound dressings because of their haemostatic properties, the mechanism being that calcium ions in the alginate exchange with sodium ions in the exudate to form a gel, and also activate the clotting cascade. Although outside the scope of the list of requirements for an ideal wound dressing given earlier haemostatic properties are of course important in a wound dressing which is to be applied to a bleeding wound. In such a dressing another property that is particularly important is the ability of the dressing to absorb exudates from the wound, especially in the form of a gel created by the action of exudate on alginate.

An early description of surgical dressings having improved haemostatic properties is contained in UK Specification No. 629 419, the dressing comprising a fibrous carrier or cotton gauze impregnated with a water-insoluble alginic material, for example alginic acid itself optionally together with a small amount of metallic alginate, preferably an insoluble alginate, such as calcium alginate. Such a dressing is likely to have poor wound release and absorption properties.

UK Patent Specification No. 1 337 931 describes an open-celled, porous, water-absorbent and waterdisintegrative sponge comprising at least one water-soluble and water-insoluble alginate. The primary use of the sponge is as a medical receptor for biological fluids, e.g. a lacteal, faecal, catamenial, surgical or dental receptor. Use of the sponge as a burn dressing is described, but not use as a wound dressing, presumably on account of the inherently disintegrative nature of the sponge when hydrated beyond 100% absorption. Being formed entirely of alginate the material cost of the sponge in high, and the production process is complex and high cost.

UK Specification No. 1 602 858 discloses a thixotropic colloidal aluminium chloride hydroxide for use in medicine, cosmetics, physical therapy and agricultural applications. For use in medicine for topical application the composition may be supported on a suitable carrier, for example a ribbon of porous polyurethane foam. Although the impregnated bandage is described as a dressing for an open wound the astringent nature of the aluminum chloride hydroxide would appear to render it unsuitable for use as a first aid dressing, and the viscous nature of the impregnated substance must detract from the absorbency of the dressing material. In one Example there is a disclosure of a form of the composition itself containing aluminum chloride hydroxide and 1 to 5% alginate. No indication is given of the intended use of this particular composition, but use in agricultural applications is to be inferred.

Alginate based haemostatic wound dressings are currently available commercially in the form of fiber mats. Such mats are not only expensive but leave a gel in the wound which has to be cleaned out, an operation which is time-consuming, probably painful for the patient, and liable to delay the healing process.

An improved and less expensive wound dressing material is proposed in UK Specification No. 2 221 620A and comprises a fibrous substrate having a discontinuous coating of a pharmaceutically-acceptable alginate deposited on a surface thereof. Because a large surface area of alginate in relation to its weight is achieved, effective haemostasis is said to be obtained with relatively small quantities of alginate. Also the levels of alginate are said to provide, surprisingly, significant wound release properties. Any fibrous material suitable for use as a wound-contracting absorbent may be used as the substrate.

It is a further aim of the present invention to provide a highly absorbent haemostatic wound dressing material which meets the previously listed seven requirements.

According to a further aspect of the present invention there is provided a wound dressing comprising an open-celled foam material impregnated with a haemostatic agent comprising a major proportion of alginic acid or a salt thereof, the impregnated material having an absorptive capacity more than 10 times its own weight. It will be appreciated that the alginate component functions not only as a haemostat but also as an absorption enhancer.

The minimum concentration of alginate required for effective haemostatic capability is about 60 $g/m^2$. Concentrations of 100 $g/m^2$ or higher are preferred.

The alginate-impregnated foam is preferably a polyurethane foam and, while it is again possible to employ a foam which has not been subjected to any surface treatment, it is preferred to employ a foam which has been surface-treated. Suitable foams for use in an alginate-impregnated haemostatic dressing are 'Lyofoam' material and the above-described polyether polyurethane foams. For use in the present invention a mixture of calcium and sodium alginates has been found most efficacious, the calcium alginate being the better haemostat but insoluble, and the sodium alginate providing the necessary element of solubility by supporting the calcium salt in suspension. The preferred range is from 70 to 90% calcium alginate and from 10 to 30 sodium alginate. At the upper limit of concentration of calcium alginate there is produced a very thick gel which is not easily absorbed by the foam during manufacture and, at the lower limit, a thin solution in which some of the calcium salt is in suspension.

Other components may, if desired, be incorporated in the foam, for example silver salts such as are commonly used for treating burn wounds: antiseptics; analgesics; and preservatives to increase the resistance of the alginate to bacterial attack.

Various methods may be employed for impregnating the foam: a thick alginate gel (for example a 70/30 Ca/Na alginate mixture in 5% (w/v) aqueous solution) may be spread on to the surface of foams and due to the thickness of the gel the concentration of the impregnated alginate is greater nearer the surface. A measured quantity of alginate solution of suitable viscosity may be applied to the surface of the foam using a syringe. Preferably, however, the foam is immersed in the alginate solution under compression and subsequently refixed before being removed from the solution and allowed to drain. Such a procedure ensures a uniform concentration of alginate through the thickness of the foam.

Whatever method of impregnation is used the foam must subsequently be dried, for example in an oven or, more preferably, due to the temperature sensitive nature of alginates, by employing a freeze-drying process.

Dressings according to the invention may take the form simply of a foam pad which is held in place over the wound by a subsequently-applied bandage or adhesive plaster in the conventional way. Alternatively the dressing may comprise one or more elements besides the foam pad, for example a strip of adhesive plaster on which the pad is mounted and extending on opposite sides thereof; or a panel of adhesive plaster extending on all sides to form an 'island dressing' (an example of such a dressing is a 'maintenance dressing' for use in industrial first aid where the primary aim is to return an operator to work with maximum protection to the wound from industrial hazards); a cohesive bandage, which is useful if the foam pad has to be applied to the wound site under pressure (an example of such a dressing is a 'transit dressing' to protect the wound and staunch more serious bleeding whilst a patient is being transported to an Accident and Emergency Center for treatment); and a layer of charcoal to absorb offensive odors given off by some wounds:

A particular example of an island dressing is one in which the backing layer is of thin, waterproof, vapor-permeable foam which allows a patient wearing the dressing to wash or shower without wetting or contaminating the wound, but which yet allows excess moisture absorbed by the pad to escape, and air to diffuse therethrough. Such a dressing is described and claimed in our co-pending UK Patent Application No. 2 228 682A.

BRIEF DESCRIPTION OF THE DRAWINGS

Although the invention may be carried out in a variety of ways, it will now be particularly illustrated in the following Examples. Reference is made to the accompanying drawings in which FIG. 1 is a diagrammatic elevation of a null head foam absorbency test apparatus;

FIG. 3 is a perspective view of a wound dressing according to the invention; and FIG. 4 is a section on the line IV—IV of FIG. 3.

DETAILED DESCRIPTION OF PREFERRED EMBODIMENTS

EXAMPLE 1

Figure 2:
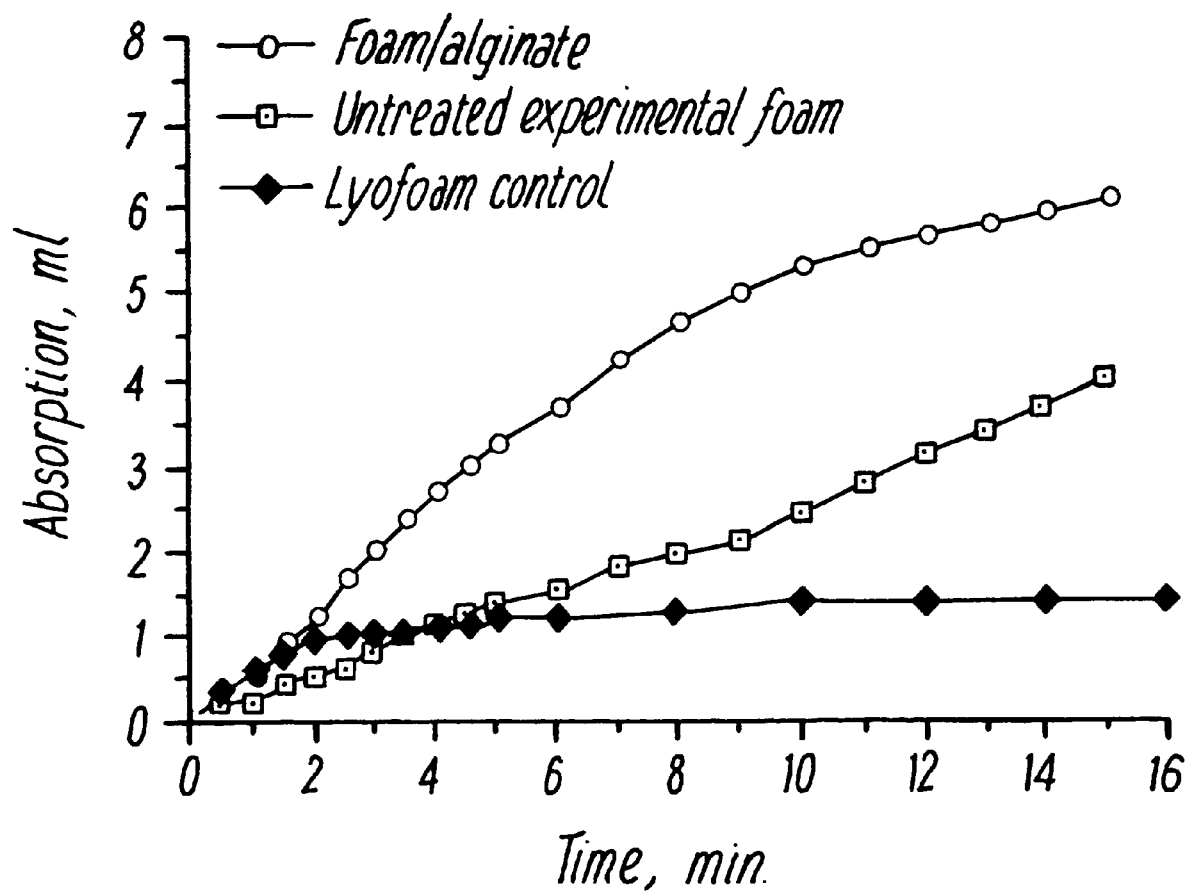
FIG. 2 is a graph showing the absorption rates of foams according to the invention and a control.

A highly absorbent polyether polyurethane foam slabstock having a density of 30 kg/m$^3$ was manufactured on conventional foam-making machinery from the following ingredients:

| Ingredients | Parts by Weight |
| --- | --- |
| Polyol 1 [Deamofen 7040 (Bayer) or Voranol CP 1421 (Dow)] | 75 |
| Polyol 2 [MW 5,000–6,000 - Deamofen 3900 (Bayer)] | 25 |
| T80/20 | 36.5 |
| DMEA | 0.05 |
| TEDA | 0.12 |
| Polysiloxane - Polyoxyalkylene block copolymer (cell stabiliser - Bayer) | 1.20 |
| Water | 3.0 |

| | Physical Test Results | | |
| --- | --- | --- | --- |
| Property | Test Method | Test Block 1 | Test Block 2 |
| Density (kg/m3) | BS4443 Pt1 | 29.8 | 30.2 |
| Hardness (N) | BS4443 Pt2 | 72 | 68 |
| Tensile Strength (kPa) | BS4443 Pt1 | 149 | 158 |
| Elongation at break (%) | BS4443 Pt1 | 530 | 530 |
| Compression Set (%) | BS4443 Pt1 | 5.7 | 5.7 |
| Porosity (l/min) | BS4443 Pt6 | 91 | 88 |

The density of the foam produced can be varied by adjustment of the water level in the above formulation.

The foam of Example 1 is also referred to subsequently as 4039/1.

EXAMPLE 2

Samples (No. 1) of the foam produced according to Example 1 were tested for their capability, under the same conditions used to produce 'Lyofoam' material as described in British Patent Specification No 1 417 962, of giving a smooth, non-adherent surface, in comparison with standard 'Lyofoam' material (Sample No. 2). The initial thickness of foam of 15 mm was chosen to give a finished thickness similar to that of 'Lyofoam' material.

Results

TABLE 1

| Sample No. | Cut Thickness (mm) | Pressing time (sec) | Pressed Thickness (mm) |
| --- | --- | --- | --- |
| 1 | 15 | 60 | 8–10 |
| 2 | 22 | 45 | 8–10 |

Absorbency Tests

Pressed samples produced as above were cut into 5 cm squares for absorbency testing. Two test methods were used:

A) BP absorbency test as follows:
1. Weigh a sample of dimensions 5 cm×5 cm accurately to four decimal places. Immerse in water for one hour, attaching a weight, if necessary, below the sample to ensure that it remains wholly immersed.
2. Remove the sample and allow to drain freely, without compression, at an angle of 45 degrees for five minutes. Reweigh the sample accurately to four decimal places, divide the increase in weight (x) by the initial weight (y) and note down the value (x/y).
3. Repeat the test four more times on four more samples and record the absorbency as an average of the five values noted down.

B) Ultra Laboratories drop absorbency test as follows:
1. Place sample on a flat surface with the smooth, absorbent surface uppermost.
2. Using a 21 G needle attached to a 2 ml syringe, allow one drop of distilled water to fall onto the sample surface from a height of approximately 8 cm. Note the time taken for the drop to be absorbed.

For test B both sides of each sample were checked to obtain an indication of whether a differential absorbency profile could be obtained to ensure that the processed surface remained wetter than the reverse.

Results

TABLE 2

| Sample | BP Absorbency (% initial sample weight) | Ultra Drop Processed Surface (Sec) | Absorbency Non-processed Surface (Sec) |
| --- | --- | --- | --- |
| 1 | 20.28 | 2 | 120 |
| 2 | Avg 10 | Avg 8 | — |

EXAMPLE 3

The procedure of Examples 1 and 2 was followed but using different types of cell stabiliser and/or different amounts thereof to produce foams of different porosities designated hereinafter as 2139/1 (Dow). 4039/3 and 4040/2 (Bayer).

EXAMPLE 4

Null Head absorbency Test.

25 mm thick samples of the foam produced in Examples 2 and 3, were cut into 10 cm squares which were tested with the null head (or constant delivery) testing apparatus shown in FIG. 1.

The apparatus 10 has a horizontally fixed "Perapex" plate 12 having a central aperture 14 of 3 mm in diameter. The aperture 16 is connected to a constant head of fluid 18 in a closed burette 20, or to a constant rate of delivery perfuser (not shown). The burette 20 has a side arm which is connected to an air bleed 22 and is supported on a platform (not shown) which can be raised or lowered by means of a screw thread to enable adjustment of the level of fluid 18. In operation, an air bleed tap 24 and the burette tap 26 are opened simultaneously, and, the fluid level adjusted to the upper edge of the aperture 14.

The apparatus 10 may be positioned at different angles of slope to identify lateral strike-through, and various pressures can be applied to determine the performance of foam dressings under compression bandaging or patient body weight.

The apparatus 10 allowed direct absorption from a liquid reservoir without 'pressure' feed to the dressing surface. Intimate contact was assured by a wet membranes interface which simulated the in vivo situation.

The test fluid was normal saline.

The pressure applied was 13.5 gf cm$^{-2}$ which for the area of sample was equivalent to 10 mm Hg. The figure was derived from readings taken below bandages, tapes, and elasticated tubular retention materials and was considered to be an acceptable experimental condition.

Method

All test materials were template cut to a circular sample, 5 cm in diameter. These were applied to the test platform and records taken of volume of fluid absorbed versus time. Readings were taken every 30 seconds for 5 minutes and then every two minutes to 10 minutes, and then again at 20 minutes.

Results

All results are averages of individual results from the numbers of samples stated in the Table 3 below.

TABLE 3

| Material<br>No. of Samples | Lyofoam<br>5 | 4039/1<br>3 | 2139/1<br>3 | 4039/3<br>3 | 4040/2<br>3 |
|---|---|---|---|---|---|
| Time (mins) | Volumes Absorbed (ml) | | | | |
| 0.0 | 0.00 | 0.00 | 0.00 | 0.00 | 0.00 |
| 0.5 | 0.35 | 0.80 | 1.00 | 0.25 | 0.30 |
| 1.0 | 0.57 | 1.33 | 1.40 | 0.35 | 0.50 |
| 1.5 | 0.76 | 1.73 | 1.70 | 0.40 | 0.70 |
| 2.0 | 0.89 | 2.10 | 1.80 | 0.50 | 0.90 |
| 2.5 | 0.96 | 2.50 | 2.00 | 0.65 | 1.00 |
| 3.0 | 0.97 | 2.82 | 2.20 | 0.70 | 1.20 |
| 3.5 | 0.97 | 3.22 | 2.40 | 0.80 | 1.40 |
| 4.0 | 1.01 | 3.57 | 2.50 | 0.85 | 1.40 |
| 4.5 | 1.02 | 3.82 | 2.60 | 0.95 | 1.60 |
| 5.0 | 1.09 | 4.03 | 2.60 | 1.00 | 1.60 |
| 6.0 | 1.18 | 4.30 | 2.70 | 1.05 | 1.80 |
| 8.0 | 1.31 | 4.93 | 3.10 | 1.25 | 2.10 |
| 10.0 | 1.42 | 5.23 | 3.10 | 1.35 | 2.40 |
| 20.0 | 1.82 | 6.93 | 3.10 | 2.05 | 3.20 |

Water Retention Capacity by B.P. Method A 228 Appendix XX Method

The whole dressing sample (of known area) was weighed and placed onto the perforated metal tray with the surface intended for wound contact in direct contact with the perforated surface.

The tray and dressing sample were then immersed (it was necessary to tie the foam samples down to the tray using an 'Ethicon' suture) in water at a temperature of 20° C. for 10 seconds. The tray and sample were then transferred to the stainless steel tank and allowed to drain freely for 10 seconds.

The metal weight was then placed onto the surface of the dressing sample such that a force of 2 kNm$^{-2}$ was applied evenly over the surface of the sample. This was left for 30 seconds and then removed carefully. The sample was then transferred immediately to a tared dish, taking care not to lose any water in the process, and weighed. The equivalent water retention capacity for an area of 100 cm$^2$ of dressing material was then calculated. The results of five determinations wore recorded and the calculated average water retention capacity is given in Table 4 below.

Results

TABLE 4

| Sample | Lyofoam Control | 4039/3 | 4040/2 | 4039/1 | 2139/1 |
|---|---|---|---|---|---|
| Avg wt of dressing (dry)/g | 3.55 | 6.39 | 6.76 | 6.31 | 6.67 |
| Avg wt of dressing (wet)/g | 15.79 | 44.26 | 37.99 | 46.61 | 46.24 |
| Wt of moisture retained/g | 12.24 | 37.87 | 31.23 | 40.30 | 39.57 |
| Moisture retention/g/g | 3.45 | 5.93 | 4.62 | 6.39 | 5.93 |
| Moisture retention/ g/100 cm$^2$ | 12.24 | 45.08 | 37.15 | 47.98 | 47.10 |

Sample Thickness Determination

One of the requirements of a wound dressing may be to provide a degree of haemostasis. If the dressing material is able to exert some pressure onto the wound, its haemostatic function will be enhanced and the healing process encouraged. The performance of the foam when under compression was assessed by measuring its thickness under load.

Apparatus

The apparatus used for this measurement was an Esadiel Thickness Gauge. The principle of operation of this equipment is that a load is applied to a sample via a presser foot. As the foot compresses the sample a circuit is broken. A dial micrometer type scale is connected to the other half of the circuit. The distance the micrometer has to be moved to make the circuit (reconnection being noted by illumination of a lamp) is then recorded as the compression of the sample.

Method

Samples of a 'Lyofoam' foam control and the foams of Examples 2 and 3 were cut to fit under the presser foot. The thickness of each sample was measured accurately. Each sample was, in turn, placed under the foot and the gauge zeroed with no load and the circuit closed. The thickness was then recorded under differing loads. As each load was added, 30 seconds were allowed for equilibration prior to measurement. Readings were taken as load was increasing and again as the load was decreased.

Since the material, in use, will often be wet, the tests were repeated with the samples having been previously soaked in water. The samples were immersed in water for 30 seconds (not under compression), removed and allowed to drain horizontally for 20 seconds prior to testing.

In order to arrive at a suitable comparison between samples, allowing for variations in original sample thickness, the results are recorded as percentages of the original thickness of the sample in Tables 5a–e.

TABLE 5a

| | Sample Thickness (% of original thickness) | | | |
|---|---|---|---|---|
| | Dry Sample | | Wet Sample | |
| Load (g/cm$^2$) | Increasing Load | Decreasing Load | Increasing Load | Decreasing Load |
| Material Under Test: Lyofoam Control | | | | |
| 0 | 100 | — | — | — |
| 20 | 71.67 | 30.25 | 50.00 | 22.25 |
| 50 | 20.44 | 16.25 | 18.63 | 15.13 |
| 100 | 17.50 | 13.13 | 15.13 | 12.25 |
| 200 | 13.50 | 11.00 | 12.50 | 10.63 |
| 500 | 10.62 | 9.25 | 9.63 | 8.75 |
| 1000 | 8.88 | 8.13 | 8.25 | 7.50 |
| 1500 | 7.50 | 7.50 | 7.25 | 7.00 |
| 2000 | 7.00 | — | 6.50 | — |
| b) Material Under Test: Foam Sample 4039/1 | | | | |
| 0 | 100 | — | — | — |
| 20 | 89.65 | 77.65 | 88.71 | 46.76 |
| 50 | 47.82 | 29.71 | 45.06 | 23.12 |
| 100 | 27.88 | 16.82 | 27.00 | 16.76 |
| 200 | 20.47 | 11.76 | 15.53 | 12.94 |
| 500 | 9.88 | 8.35 | 11.18 | 9.71 |
| 1000 | 7.88 | 7.06 | 8.82 | 8.12 |
| 1500 | 6.82 | 6.47 | 7.71 | 7.24 |
| 2000 | 6.24 | — | 6.88 | — |
| c) Material Under Test: Foam Sample 4039/3 | | | | |
| 0 | 100 | — | — | — |
| 20 | 89.72 | 75.72 | 91.00 | 41.44 |
| 50 | 49.17 | 28.06 | 38.33 | 23.06 |
| 100 | 22.50 | 16.17 | 20.94 | 16.44 |
| 200 | 14.67 | 11.33 | 15.11 | 12.39 |
| 500 | 9.39 | 7.89 | 10.11 | 8.94 |
| 1000 | 7.22 | 6.50 | 7.89 | 7.33 |
| 1500 | 6.33 | 5.83 | 6.94 | 6.61 |
| 2000 | 5.56 | — | 6.28 | — |
| d) Material Under Test: Foam Sample 2139/1 | | | | |
| 0 | 100 | — | — | — |
| 20 | 87.16 | 70.84 | 86.53 | 37.39 |
| 50 | 53.11 | 27.84 | 38.00 | 22.37 |
| 100 | 21.79 | 16.11 | 20.58 | 15.95 |
| 200 | 13.68 | 11.32 | 14.68 | 12.00 |
| 500 | 9.21 | 8.21 | 10.16 | 9.00 |
| 1000 | 7.42 | 6.74 | 8.21 | 7.53 |
| 1500 | 6.47 | 6.26 | 7.16 | 6.84 |
| 2000 | 5.95 | — | 6.58 | — |
| e) Material Under Test: Foam Sample 4040/2 | | | | |
| 0 | 100 | — | — | — |
| 20 | 87.93 | 72.94 | 89.99 | 42.17 |
| 50 | 58.50 | 29.94 | 51.94 | 22.72 |
| 100 | 25.56 | 17.78 | 22.28 | 16.67 |
| 200 | 16.22 | 12.33 | 16.50 | 12.72 |
| 500 | 10.78 | 8.78 | 11.00 | 9.44 |
| 1000 | 8.17 | 7.19 | 8.72 | 7.77 |
| 1500 | 7.17 | 6.72 | 7.67 | 7.28 |
| 2000 | 6.39 | — | 6.89 | — |

From the results of the above tests it is apparent that the foam of Example 3 shows great improvement over the standard 'Lyofoam' product. The demand absorbency is over 3.5 times higher (3536 g/m$^2$ against 929 g/m$^2$ for 'Lyofoam' at 20 minutes).

The fluid retention capacity is greatly increased (5.93 g fluid/g against 3.45 g/g for 'Lyofoam'); and the thickness under compression is increased from 70% to 90% (dry) and from 30% to 78% (wet). This last result means that under equal compression from bandages, the material of Example 2 is capable of exerting a greater pressure on the wound base, thus helping the clotting process.

EXAMPLE 5

A backing layer was provided on the foam sheet of Example 2 by laminating to the back (untreated) surface thereof a 3 mm thick peeled polyester urethane sheet (K26-Kay Metzeler). The adherence was comparable to that with 'Lyofoam' material.

Samples of foam with the backing layer were tested for water vapor permeability using BP Method A224 Appendix XXJ2. They were found to have a vapor permeability of 2450 g/m$^2$/24 hrs which is comparable to the average figure of around 2800 g/m$^2$/24 hrs obtained with 'Lyofoam' material.

EXAMPLE 6

The foam of Example 3 was impregnated with alginate using a 90/10 Ca/Na alginate solution (10% w/v in water), as follows:

Test samples of the foam sheet 4.5×4.5 cm (20.25 cm$^{-2}$) were weighed (W1). The thickness of the foam was measured using the Essdiel Thickness Gauge at minimum pressure 4.2 gf/cm$^2$. Each test sample was immersed in the alginate solution and compressed for one minute under a pressure of 16.6 gf cm$^{-2}$. The pressure was removed and the sample allowed to remain in the solution for a further minute. The impregnated foam was then allowed to drain freely on a perforated tray for one minute. The excess solid matter was removed from the surface of the sample which was then reweighed (W2). The treated samples were dried in a fan oven at 50° for 18 hours and allowed to cool at ambient temperature before reweighing (W3). The following values were calculated:

The weight of solution absorbed, W4=W2−W1.
The dry weight of alginate retained, W5=W3−W1.
The alginate retained $$g/g = \frac{W5}{W1}$$

The foam impregnation weights in grams are shown in the following Table 6.

TABLE 6

| Test No | Wtm$^{-2}$ | W1 | W2 | W3 | W4 | W5 |
|---|---|---|---|---|---|---|
| 1. | 593.1 | 1.201 | 7.013 | 1.630 | 5.812 | 0.429 |
| 2. | 661.7 | 1.340 | 6.889 | 1.736 | 5.549 | 0.396 |
| 3. | 718.0 | 1.454 | 7.501 | 1.899 | 6.047 | 0.445 |
| 4. | 704.2 | 1.426 | 6.929 | 1.853 | 5.503 | 0.427 |
| 5. | 697.8 | 1.220 | 7.851 | 1.718 | 6.631 | 0.498 |
| 6. | 602.5 | 1.237 | 8.295 | 1.752 | 7.058 | 0.515 |
| 7. | 610.9 | 1.222 | 7.316 | 1.674 | 6.094 | 0.454 |
| 8. | 603.5 | 1.300 | 7.683 | 1.717 | 6.383 | 0.417 |
| MEAN | 652.96 | 1.30 | 7.434 | 1.747 | 6.134 | 0.448 |
| S.d. | 50.4 | 0.098 | 0.496 | 0.089 | 0.537 | 0.041 |

The alginate-impregnated foam product was then tested for demand absorbency rate using the apparatus of FIG. 1, as previously described, for a period of 15 minutes using C.9% saline solution at ambient temperature. The final weight of the foam samples W6 was used to calculate the absorbency $$g/g = \frac{W6}{W3}$$

The absorbency rates of the alginate impregnated material, unimpregnated material and a 'Lyofoam' control are shown in FIG. 2.

EXAMPLE 7

FIGS. 3 and 4 show an 'island' dressing of the type described and claimed in UK Patent Application No. 2 228 682A. The dressing 30 comprises a pad 32 formed of the foam of Example 2 presenting a smooth, compressed surface layer 34 and a backing layer 36 of a thin, waterproof, soft, conformable, vapor-permeable polyether foam having a layer 38 of vapor-permeable adhesive coated thereon, which serves both to adhere the dressing 30 to a patient and to the perimeter of the back of the pad 32. Interposed between the central area of the pad 32 and the backing layer 36 is a layer 40 of non-woven fibers impregnated with granules of activated carbon for the absorption of offensive odor given off by certain types of wound. Before application the exposed adhesive layer 38 and surface layer 34 are protected by removable panels 42,44 of low-adherent film or silicone-coated release paper.

We claim:

1. A wound dressing comprising a physiologically compatible, open-celled, hydrophilic polyether polyurethane foam derived from a foamable composition comprising a polyether polyol component containing ethylene oxide groups and having an absorptive capacity greater than 10 times its own weight, as determined when foam cells adjacent one surface of the foam material have been irreversibly partially collapsed relative to foam cells remote from the said surface.

2. A dressing as claimed in claim 1, in which said foam material is derived from a foamable composition comprising a polyol component constituted by a polyether polyol containing ethylene oxide groups and a branched ethylene oxide modified polyether polyol in a ratio of from 65 to 85:35 to 15 parts by weight.

3. A dressing as claimed in claim 1 in which said foam material also comprises an impregnated haemostatic composition comprising a major proportion of an impregnant alginic acid and the salts thereof.

4. A dressing as carried in claim 3, in which said haemostatic composition comprises calcium alginate and sodium alginate in a ratio of from 90 to 70:10 to 30 parts by weight.

5. A dressing as claimed in claim 3, in which the haemostatic composition is present in an amount of at least 60 g/m$^2$ on a dry basis.

6. A dressing as claimed in claim 1, in which foam cells adjacent one surface of the foam material are irreversibly partially collapsed relative to foam cells remote from said surface to reduce adherency to a healing wound.

7. A dressing as claimed in claim 1 and further comprising a gas- and moisture-permeable backing layer for the exclusion of bacteria.

8. A dressing as claimed in claim 1 in which said foam material is in the form of a pad and which further comprises an adhesive sheet or panel strip extending over the back of said pad and beyond at least part of the perimeter thereof.

9. A dressing as claimed in claim 8 and further comprising a layer, of absorbent for offensive odor emanating from a wound.

10. A method of dressing a wound comprising the step of applying to the wound a physiologically compatible, open-celled, hydrophilic polyether polyurethane foam material derived from a foamable composition comprising a polyether polyol component containing ethylene oxide groups and having an absorptive capacity greater than 10 times its own weight, as determined when foam cells adjacent one surface of the foam material have been irreversibly partially collapsed relative to foam cells remote from the said surface.

11. A method as claimed in claim 10, in which said foam material is derived from a foamable composition comprising a polyol component constituted by a polyether polyol containing ethylene oxide groups and a branched ethylene oxide modified polyether polyol in a ratio of from 65 to 85:35 to 15 parts by weight.

12. A method as claimed in claim 1, in which said foam material also comprises an impregnated haemostatic composition comprising a major proportion of an impregnant selected from the group consisting of alginic acid and the salts thereof.

13. A method as claimed in claim 12, in which said haemostatic composition comprises calcium alginate and sodium alginate in a ratio of from 90 to 70:10 to 30 parts by weight.

14. A method as claimed in claim 12, in which the haemostatic composition is present in an amount of at least 60 g/m$^2$ on a dry basis.

15. A method as claimed in claim 10, in which foam cells adjacent one surface of the foam material are irreversibly partially collapsed relative to foam cells remote from said surface to reduce adherency to a healing wound.

16. A method as claimed in claim 10, in which said foam material further comprises a gas- and moisture-permeable backing layer for the exclusion of bacteria.

17. A method as claimed in claim 10, in which said foam material is in the form of a pad and further comprises an adhesive sheet or panel strip extending over the back of said pad and beyond at least part of the perimeter thereof.

18. A method as claimed in claim 17, in which said pad further comprises a layer of absorbent for offensive odor emanating from said wound.

* * * * *